(12) United States Patent
Malle et al.

(10) Patent No.: US 8,790,625 B2
(45) Date of Patent: Jul. 29, 2014

(54) POLYCONDENSATE, COMPOSITION CONTAINING A POLYCONDENSATE, METHOD OF TREATMENT, AND METHOD OF PREPARATION

(75) Inventors: Gerard Malle, Villiers S/Morin (FR); Jean Mondet, Aulnay sous Bois (FR); Xavier Blin, Paris (FR); Ivan Rodriguez, Cauffry (FR); Pascal Giustiniani, Levallois Perret (FR)

(73) Assignee: L'Oreal, Paris (FR)

( * ) Notice: Subject to any disclaimer, the term of this patent is extended or adjusted under 35 U.S.C. 154(b) by 816 days.

(21) Appl. No.: 11/766,118

(22) Filed: Jun. 21, 2007

(65) Prior Publication Data

US 2008/0152607 A1 Jun. 26, 2008

Related U.S. Application Data

(60) Provisional application No. 60/817,073, filed on Jun. 29, 2006.

(30) Foreign Application Priority Data

Jun. 22, 2006 (FR) ...................................... 06 52591

(51) Int. Cl.
*A61K 8/72* (2006.01)
*C08F 283/00* (2006.01)
*A61Q 5/00* (2006.01)
*A61Q 1/06* (2006.01)
*A61Q 1/10* (2006.01)
*A61Q 1/00* (2006.01)

(52) U.S. Cl.
USPC ......... 424/64; 525/418; 424/78.08; 424/70.6; 424/70.7; 424/63

(58) Field of Classification Search
None
See application file for complete search history.

(56) References Cited

U.S. PATENT DOCUMENTS

| 2,915,488 | A | 12/1959 | Kraft et al. |
| 4,368,294 | A * | 1/1983 | Deubzer et al. ............... 525/100 |
| 5,585,104 | A * | 12/1996 | Ha et al. ........................ 424/401 |
| 2006/0062752 | A1 * | 3/2006 | Gotou et al. ............... 424/70.31 |
| 2010/0239509 | A1 | 9/2010 | Chodorowski-Kimmes et al. |
| 2010/0272660 | A1 | 10/2010 | Malle |

FOREIGN PATENT DOCUMENTS

| JP | 61-176668 | 8/1986 |
| JP | 4-145014 | 5/1992 |

OTHER PUBLICATIONS

Determination of Hydroxyl Number in Polymers by Infrared Spectroscopy, Lee et al Applied Spectroscopy, vol. 44, iss 10 pp. 1595-1722 (Dec. 1990) abstract only provided.*
Lin, KF; "Paints, Varnishes, and Related Products" Chapter 9 in Bailey's industrial Oil and Fat Products, Sixth Edition, 2005, edited by F. Shahidi, pp. 307-351.*
Database WPI Week 198808, Derwent Publications Ltd., London, GB; AN 1988-052800 XP002417277 & JP 63 008318 (Kobayashi Kose KK), Jan. 14, 1988.
Database WPI Week 197814, Derwent Publications Ltd., London, GB; AN 1978-26140A XP002409236 & JP 53 018742 (Kanebo Ltd.) Feb. 21, 1978.
Database WPI Week 198312, Derwent Publications Ltd., London, GB; AN 1983-28350K XP002417278 & JP 58 023614 (Asanuma Kogyo KK), Feb. 12, 1983.
Database WPI Week 197910, Derwent Publications Ltd., London, GB: AN 1979-18769B XP002423623 & JP 54 011244 (Kanebo Ltd.), Jan. 27, 1979.
U.S. Appl. No. 11/693,842, filed Mar. 3, 2007, Rodriguez, et al.
U.S. Appl. No. 60/948,495, filed Jul. 9, 2007, Giustiniani, et al.
U.S. Appl. No. 12/142,413, filed Jun. 19, 2008, Giustiniani, et al.
Office Action issued May 8, 2005 in JP Application No. 2007-164385 (English Translation).

* cited by examiner

*Primary Examiner* — Ernst V Arnold
*Assistant Examiner* — Jianfeng Song
(74) *Attorney, Agent, or Firm* — Oblon, Spivak, McClelland, Maier & Neustadt, L.L.P.

(57) ABSTRACT

The present application relates to a polycondensate that can be obtained by reaction:

of polyol containing 3 to 6 hydroxyl groups;

of non-aromatic, saturated or unsaturated monocarboxylic acid;

of aromatic monocarboxylic acid containing 7 to 11 carbon atoms; and of polycarboxylic acid, saturated or unsaturated, or even aromatic, linear, branched and/or cyclic, containing at least 2 carboxyl groups COOH; and/or a cyclic anhydride of such a polycarboxylic acid.

The application also relates to a method of cosmetic treatment employing said composition, the polycondensate thus defined and a method of preparation of the polycondensate.

41 Claims, No Drawings

POLYCONDENSATE, COMPOSITION CONTAINING A POLYCONDENSATE, METHOD OF TREATMENT, AND METHOD OF PREPARATION

REFERENCE TO PRIOR APPLICATIONS

This application claims priority to U.S. provisional application 60/817,073 filed Jun. 29, 2006, and to French patent application 0652591 filed Jun. 22, 2006, both incorporated herein by reference.

FIELD OF THE INVENTION

The present invention relates to novel polymers of the polycondensate family, of modified alkyd type, as well as to their use in compositions, notably in cosmetic compositions such as lipsticks, to compositions containing them, and to methods of preparation of said polycondensates.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

There are a great many cosmetic compositions for which properties of gloss of the deposited film, after application on keratinous materials (skin, lips, integumentary appendages), are desired. We may mention for example lipsticks, nail varnish or also certain hair-care products.

In order to obtain such a result, it is possible to combine particular raw materials, notably lanolins, with so-called gloss oils, such as the polybutenes, which however have high viscosity; or esters of acids or of fatty alcohols with a high number of carbons; or certain vegetable oils; or esters resulting from the partial or total esterification of a hydroxylated aliphatic compound with an aromatic acid, as described in patent application EP1097699.

It is also known to combine lanolins with polyesters obtained by a multi-step reaction of castor oil with isostearic acid and then with succinic acid, as described in U.S. Pat. No. 6,342,527.

To improve the gloss of the deposited film, as well as its durability, it has also been proposed to use esters resulting from the condensation of a polyol with a carboxylic acid of the "neo" type, notably in FR2838049.

EP1457201 describes a composition that combines a polyester of hydroxylated carboxylic acid triglycerides and an oil of low molecular weight selected from polybutylenes, hydrogenated polyisobutylenes, hydrogenated or unhydrogenated polydecenes, vinylpyrrolidone copolymers, esters of linear fatty acids, hydroxylated esters, esters of fatty alcohols or of $C_{24}$-$C_{28}$ branched fatty acids, silicone oils and/or oils of vegetable origin.

Patent application EP0792637 describes a composition combining an aromatic ester and a polymer of the polybutene or polyisobutene type. Patent application EP1155687 describes a method comprising incorporating, in an oil phase comprising a cosmetically acceptable oil, an organopolysiloxane having at least 2 groups capable of forming hydrogen bonds.

However, even if these compositions and combinations improve gloss significantly, they are still deemed inadequate with respect to long durability of said gloss, over time.

SUMMARY OF THE INVENTION

The aim of the present invention is to provide novel polymers which can impart significant gloss to a, notably film-forming, deposit, while maintaining good durability of said gloss over time; this can find particularly advantageous application in the area of lipsticks. Moreover, polymers are also provided that can in addition advantageously endow the composition with excellent durability over time on keratinous materials, notably on the lips.

The alkyd resins constitute a particular class of polyesters as the product of reaction of polyols and polycarboxylic acids, generally modified with unsaturated fatty acids, such as oleic acid, or with unsaturated oils, for example soya oil or castor oil, which make it possible to adjust their film-forming properties, notably their drying rate, their hardness, and their strength.

Thus, U.S. Pat. No. 2,915,488 proposed modified alkyd resins in which a proportion of the fatty acids obtained from soya oil has been replaced with benzoic acid. These novel resins display improved properties in terms of resistance to alkalies and detergents; the films containing them dry faster and are harder. However, no application, notably cosmetic or topical, has been envisaged for these resins.

Moreover, the fatty acids present in soya oil mainly comprise two unsaturated fatty acids: about 55% linoleic acid (C18:2) and 28% oleic acid (C18:1), according to "Surface Coatings Science and Technology", 2nd edition, JOHN WILEY & Sons, pages 104 and 105. Now, it is known that some unsaturated fatty acids can, in time, undergo autooxidation which can cause rancidity, and can lead to problems of storage of compositions containing these raw materials. Furthermore, the alkyd resins described in U.S. Pat. No. 2,915, 488, which contain a high proportion of linoleic and oleic fatty acids, are not optimal, in particular in terms of stability, for use in cosmetics.

The crosslinking of alkyd resins by oxidation in the air with formation of hydroperoxides has a crucial role in the drying rate of the film, and, consequently, in its final properties of hardness and resistance to external aggressive factors. In the usual fields of application of these alkyd resins, namely paints, the rate of crosslinking, and therefore of drying, is generally accelerated by adding particular metal salts, called "driers", such as the naphthenates and octanoates of cobalt which speed up the decomposition of the hydroperoxides; this is notably described in Principles of Polymerization, 4th edition, JOHN WILEY & SONS, pages 737-738 and also in Surface Coatings Science and Technology, 2nd edition, JOHN WILEY & SONS, tables 2.3 and 2.4, pages 526-530. However, the use of these metal salts is clearly undesirable in cosmetics for obvious reasons of toxicity.

Moreover, most of the alkyd resins do not have suitable solubility in the oily media usually employed in cosmetics, such as vegetable oils, alkanes, fatty esters, fatty alcohols, silicone oils, and notably comprising isododecane, Parleam, isononyl isononanoate, octyl dodecanol, phenyl trimethicone, $C_{12}$-$C_{15}$ alkyl benzoate and/or D5 (decamethylcyclopentasiloxane).

After much research, the inventors discovered, surprisingly and unexpectedly, that certain polycondensates with a high content of particular carboxylic acids, including non-aromatic monocarboxylic acids, lead to improved performance in terms of gloss, maintenance of said gloss, and in addition long durability of the film obtained, but can be carried in the usual cosmetic media, notably the usual oily cosmetic media.

The present invention therefore relates to a composition comprising, preferably in a cosmetically or pharmaceutically acceptable medium, at least one polycondensate that can be obtained by reaction:
- of 10 to 30 wt. %, relative to the total weight of the polycondensate, of at least one polyol containing 3 to 6 hydroxyl groups;
- of 30 to 80 wt. %, relative to the total weight of the polycondensate, of at least one saturated or unsaturated, linear, branched and/or cyclic, non-aromatic monocarboxylic acid, containing 6 to 32 carbon atoms;
- of 0.1 to 10 wt. %, relative to the total weight of the polycondensate, of at least one aromatic monocarboxylic acid containing 7 to 11 carbon atoms, optionally in addition substituted with 1 to 3 saturated or unsaturated, linear, branched and/or cyclic alkyl radicals, which contain 1 to 32 carbon atoms;
- of 5 to 40 wt. %, relative to the total weight of the polycondensate, of at least one polycarboxylic acid, saturated or unsaturated, or even aromatic, linear, branched and/or cyclic, containing at least 2 carboxyl groups COOH, notably 2 to 4 COOH groups; and/or a cyclic anhydride of such a polycarboxylic acid.

Preferably, the composition comprises a polycondensate as defined above, provided that the polycondensate is obtained by reaction:
- of 10 wt. % of at least one aromatic monocarboxylic acid containing 7 to 11 carbon atoms, optionally in addition substituted with 1 to 3 saturated or unsaturated, linear, branched and/or cyclic alkyl radicals, which contain 1 to 32 carbon atoms; and
- of 15 to 30 wt. %, relative to the total weight of the polycondensate, of at least one polyol containing 3 to 6 hydroxyl groups; and
- of 30 to 40 wt. %, relative to the total weight of the polycondensate, of at least one saturated or unsaturated, linear, branched and/or cyclic, non-aromatic monocarboxylic acid, containing 6 to 32 carbon atoms; and
- of 10 to 25 wt. %, relative to the total weight of the polycondensate, of at least one polycarboxylic acid, saturated or unsaturated, or even aromatic, linear, branched and/or cyclic, containing at least 2 carboxyl groups COOH, notably 2 to 4 COOH groups; and/or a cyclic anhydride of such a polycarboxylic acid; these conditions being cumulative, and the ratio of the number of moles of aromatic monocarboxylic acid to the number of moles of non-aromatic monocarboxylic acid is between 0.08 and 0.70.

Preferably, the composition comprises a polycondensate as defined above, provided that when the polycondensate contains 10 wt. % of at least one aromatic monocarboxylic acid containing 7 to 11 carbon atoms, optionally in addition substituted with 1 to 3 saturated or unsaturated, linear, branched and/or cyclic alkyl radicals, which contain 1 to 32 carbon atoms; then the ratio of the number of moles of aromatic monocarboxylic acid to the number of moles of non-aromatic monocarboxylic acid is between 0.08 and 0.70.

Another object of the invention is a polycondensate that can be obtained by reaction:
- of 10 to 30 wt. %, relative to the total weight of the polycondensate, of at least one polyol containing 3 to 6 hydroxyl groups;
- of 45 to 80 wt. %, relative to the total weight of the polycondensate, of at least one saturated, linear, branched and/or cyclic non-aromatic monocarboxylic acid, containing 6 to 32 carbon atoms;
- of 0.1 to 10 wt. %, relative to the total weight of the polycondensate, of at least one aromatic monocarboxylic acid containing 7 to 11 carbon atoms, optionally in addition substituted with 1 to 3 saturated or unsaturated, linear, branched and/or cyclic alkyl radicals, which contain 1 to 32 carbon atoms;
- of 5 to 40 wt. %, relative to the total weight of the polycondensate, of at least one polycarboxylic acid, saturated or unsaturated, or even aromatic, linear, branched and/or cyclic, containing at least 2 carboxyl groups COOH, notably 2 to 4 COOH groups; and/or a cyclic anhydride of such a polycarboxylic acid.

Notably, the compositions have good application properties and good covering power; good adherence to the substrate, whether the nails, the hair, the eyelashes, the skin or the lips; flexibility and sufficient strength of the film, to prevent cracking, for example in the case of varnish or lipsticks; as well as an excellent level of long-lasting gloss.

The properties of comfort and of slip are also very satisfactory.

These polycondensates can easily be carried in solvent or oily cosmetic media, notably oils, fatty alcohols and/or fatty esters, which makes them easier to use in the cosmetic field, notably in lipsticks or foundations.

The polycondensates according to the invention can be prepared easily, in a single stage of synthesis, and without producing waste products, and moreover at low cost.

Furthermore, it is easily possible to modify the structure and/or the properties of the polycondensates according to the invention, by varying the chemical nature of the various ingredients and/or their proportions, in view of the present disclosure.

The polycondensates according to the invention are advantageously branched; this makes it possible to generate a network by entanglement of the polymer chains, and therefore obtain preferred properties, notably in terms of improved durability and improved gloss, and in terms of solubility. It was found in fact that the linear polycondensates do not provide a highly desirable improvement in durability of the composition, and that the polycondensates of the dendrimer type, which have regular chains, do not display optimum solubility.

The polycondensates according to the invention are polycondensates of the alkyd type, and can therefore be obtained by esterification/polycondensation, according to methods known by a person skilled in the art, of the constituents described below.

One of the constituents required for preparation of the polycondensates according to the invention is a compound containing 3 to 6 hydroxyl groups (polyol), notably 3 to 4 hydroxyl groups. It is of course possible to use a mixture of said polyols.

Said polyol can notably be a carbon compound, notably a hydrocarbon compound, linear, branched and/or cyclic, saturated or unsaturated, containing 3 to 18 carbon atoms, notably 3 to 12, or even 4 to 10 carbon atoms, and 3 to 6 hydroxyl groups (OH), and can contain in addition one or more oxygen atoms inserted in the chain (ether function).

Said polyol is preferably a saturated, linear or branched hydrocarbon compound, containing 3 to 18 carbon atoms, notably 3 to 12, or even 4 to 10 carbon atoms, and 3 to 6 hydroxyl groups (OH).

It can for example be selected from, alone or mixed:
- triols, such as 1,2,4-butanetriol, 1,2,6-hexanetriol, trimethylolethane, trimethylolpropane, glycerol;
- tetraols, such as pentaerythritol (tetramethylolmethane), erythritol, diglycerol or ditrimethylolpropane;
- pentols such as xylitol;
- hexyls such as sorbitol and mannitol; or dipentaerythritol or triglycerol.

Preferably, the polyol is selected from glycerol, pentaerythritol, diglycerol, sorbitol and mixtures thereof; and more preferably it is pentaerythritol.

The polyol, or the polyol mixture, preferably represents 10 to 30 wt. %, notably 12 to 25 wt. %, and more preferably 14 to 22 wt. %, of the total weight of the final polycondensate.

Another constituent required for preparation of the polycondensates according to the invention is a saturated or unsaturated, linear, branched and/or cyclic, non-aromatic monocarboxylic acid, containing 6 to 32 carbon atoms, notably 8 to 28 carbon atoms and preferably 10 to 24, or even 12 to 20, carbon atoms. It is of course possible to use a mixture of said non-aromatic monocarboxylic acids.

By non-aromatic monocarboxylic acid, we mean a compound of formula RCOOH, in which R is a saturated or unsaturated, linear, branched and/or cyclic hydrocarbon radical, containing 5 to 31 carbon atoms, notably 7 to 27 carbon atoms, and preferably 9 to 23 carbon atoms, or even 11 to 19 carbon atoms.

Preferably, radical R is saturated. More preferably, said radical R is linear or branched, and preferably of $C_5$-$C_{31}$, or even of $C_{11}$-$C_{21}$.

In a specific embodiment of the invention, the nonaromatic monocarboxylic acid preferably exhibits a melting point of greater than or equal to 25° C., notably of greater than or equal to 28° C., or even 30° C.; this is because it has been found that, when such an acid is employed, in particular in a large amount, it is possible, first, to obtain good gloss and the durability of said gloss and, secondly, to reduce the amount of waxes normally present in the composition envisaged.

Among the non-aromatic monocarboxylic acids that can be used, mention may be made by way of example of, alone or mixed:
- saturated monocarboxylic acids such as caproic acid, caprylic acid, isoheptanoic acid, 4-ethylpentanoic acid, 2-ethylhexanoic acid, 4,5-dimethylhexanoic acid, 2-heptylheptanoic acid, 3,5,5-trimethylhexanoic acid, octanoic acid, isooctanoic acid, nonanoic acid, decanoic acid, isononanoic acid, lauric acid, tridecanoic acid, myristic acid, palmitic acid, stearic acid, isostearic acid, arachidic acid, behenic acid, cerotic (hexacosanoic) acid; cyclopentanecarboxylic acid, cyclopentaneacetic acid, 3-cyclopentyl-propionic acid, cyclohexanecarboxylic acid, cyclohexylacetic acid, 4-cyclohexylbutyric acid;
- unsaturated but non-aromatic monocarboxylic acids, such as caproleic acid, obtusilic acid, undecylenic acid, dodecylenic acid, linderic acid, myristoleic acid, physeteric acid, tsuzuic acid, palmitoleic acid, oleic acid, petroselinic acid, vaccenic acid, elaidic acid, gondoic acid, gadoleic acid, erucic acid, cetoleic acid, nervonic acid, linoleic acid, linolenic acid, arachidonic acid.

Mention may be made by way of example, among nonaromatic monocarboxylic acids having a melting point of greater than or equal to 25° C., of, alone or as a mixture:
- among saturated monocarboxylic acids: decanoic (capric) acid, lauric acid, tridecanoic acid, myristic acid, palmitic acid, stearic acid, arachidic acid, behenic acid, cerotic (hexacosanoic) acid;
- among unsaturated but nonaromatic monocarboxylic acids: petroselinic acid, vaccenic acid, elaidic acid, gondoic acid, gadoleic acid, erucic acid, nervonic acid.

Preferably, it is possible to use 2-ethylhexanoic acid, isooctanoic acid, lauric acid, myristic acid, isoheptanoic acid, isononanoic acid, nonanoic acid, palmitic acid, isostearic acid, stearic acid, behenic acid, and mixtures thereof, and even more preferably, isostearic acid alone or stearic acid alone.

Said non-aromatic monocarboxylic acid, or the mixture of said acids, represents preferably 30 to 80 wt. %, notably 40 to 75 wt. %, or even 45 to 70 wt. %, and better still 50 to 65 wt. %, of the total weight of the final polycondensate.

Another constituent required for preparation of the polycondensates according to the invention is an aromatic monocarboxylic acid containing 7 to 11 carbon atoms, optionally in addition substituted with 1 to 3 saturated or unsaturated, linear, branched and/or cyclic alkyl radicals, which contain 1 to 32 carbon atoms, notably 2 to 12, or even 3 to 8 carbon atoms.

It is of course possible to use a mixture of said aromatic monocarboxylic acids.

By aromatic monocarboxylic acid, we mean a compound of formula R'COOH, in which R' is an aromatic hydrocarbon radical, containing 6 to 10 carbon atoms, and in particular the benzoic and naphthoic radicals. Said radical R' can in addition be substituted with 1 to 3 saturated or unsaturated, linear, branched and/or cyclic alkyl radicals, containing 1 to 32 carbon atoms, notably 2 to 12, or even 3 to 8 carbon atoms; and notably selected from methyl, ethyl, propyl, isopropyl, butyl, isobutyl, tert-butyl, pentyl, isopentyl, neopentyl, cyclopentyl, hexyl, cyclohexyl, heptyl, isoheptyl, octyl or isooctyl.

Among the aromatic monocarboxylic acids that can be used, we may mention by way of example, alone or mixed, benzoic acid, o-toluic acid, m-toluic acid, p-toluic acid, 1-naphthoic acid, 2-naphthoic acid, 4-tert-butyl-benzoic acid, 1-methyl-2-naphthoic acid, 2-isopropyl-1-naphthoic acid.

Preferably, it is possible to use benzoic acid, 4-tert-butyl-benzoic acid, o-toluic acid, m-toluic acid, 1-naphthoic acid, alone or mixed; and better still, benzoic acid alone.

Said aromatic monocarboxylic acid, or the mixture of said acids, represents preferably 0.1 to 10 wt. %, notably 0.5 to 9.95 wt. %, better still 1 to 9.5 wt. %, or even 1.5 to 8 wt. %, of the total weight of the final polycondensate.

Another constituent required for preparation of the polycondensates according to the invention is a polycarboxylic acid, saturated or unsaturated, or even aromatic, linear, branched and/or cyclic, containing at least 2 carboxyl groups COOH, notably 2 to 4 COOH groups; and/or a cyclic anhydride of such a polycarboxylic acid. It is of course possible to use a mixture of said polycarboxylic acids and/or anhydrides.

Said polycarboxylic acid can notably be selected from the linear, branched and/or cyclic, saturated or unsaturated, or even aromatic, polycarboxylic acids, containing 2 to 50, notably 2 to 40, carbon atoms, in particular 3 to 36, or even 3 to 18, and better still 4 to 12 carbon atoms, or even 4 to 10 carbon atoms; said acid has at least two carboxyl groups COOH, preferably from 2 to 4 COOH groups.

Preferably, said polycarboxylic acid is aliphatic saturated, linear and has 2 to 36 carbon atoms, notably 3 to 18 carbon atoms, or even 4 to 12 carbon atoms; or it is aromatic and has 8 to 12 carbon atoms. It preferably has 2 to 4 COOH groups.

Said cyclic anhydride of such a polycarboxylic acid can notably correspond to one of the following formulae:

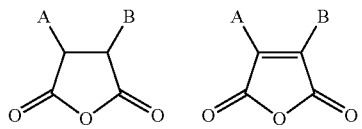

in which groups A and B are, independently of one another:
a hydrogen atom;
an aliphatic, saturated or unsaturated, linear, branched and/or cyclic, or alternatively aromatic, carbon radical; containing 1 to 16 carbon atoms, notably 2 to 10 carbon atoms, or even 4 to 8 carbon atoms, notably methyl or ethyl;
or alternatively A and B, taken together, form a ring having a total of 5 to 7, notably 6 carbon atoms, saturated or unsaturated, or even aromatic.

Preferably, A and B represent a hydrogen atom or together form an aromatic ring having a total of 6 carbon atoms.

Among the polycarboxylic acids or their anhydrides that can be used, we may mention, alone or mixed:
dicarboxylic acids such as decanedioic acid, dodecanedioic acid, cyclopropanedicarboxylic acid, cyclohexanedicarboxylic acid, cyclobutanedicarboxylic acid, naphthalene-1,4-dicarboxylic acid, naphthalene-2,3-dicarboxylic acid, naphthalene-2,6-dicarboxylic acid, suberic acid, oxalic acid, malonic acid, succinic acid, phthalic acid, terephthalic acid, isophthalic acid, tetrahydrophthalic acid, hexahydrophthalic acid, pimelic acid, sebacic acid, azelaic acid, glutaric acid, adipic acid, fumaric acid, maleic acid, itaconic acid, dimers of fatty acids (notably of $C_{36}$) such as products marketed under the names Pripol 1006, 1009, 1013 and 1017, by Uniqema;
tricarboxylic acids such as cyclohexanetricarboxylic acid, trimellitic acid, 1,2,3-benzenetricarboxylic acid, 1,3,5-benzenetricarboxylic acid;
tetracarboxylic acids such as butanetetracarboxylic acid and pyromellitic acid;
the cyclic anhydrides of these acids and notably phthalic anhydride, trimellitic anhydride, maleic anhydride and succinic anhydride.

Preferably, it is possible to use adipic acid, phthalic anhydride and/or isophthalic acid, and better still isophthalic acid alone.

Said polycarboxylic acid and/or its cyclic anhydride represents preferably 5 to 40 wt. %, notably 10 to 30 wt. %, and better still 14 to 25 wt. %, of the total weight of the final polycondensate.

The polycondensate according to the invention can in addition comprise a silicone with hydroxyl (OH) and/or carboxyl (COOH) functions.

It can contain 1 to 3 hydroxyl and/or carboxyl functions, and preferably has two hydroxyl functions or alternatively two carboxyl functions.

These functions can be located at the end of the chain or within the chain, but advantageously at the end of the chain.

It is preferable to use silicones having a weight-average molecular weight (Mw) between 300 and 20 000, notably 400 and 10 000, or even 800 and 4000.

This silicone can be of formula:

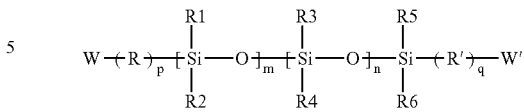

in which:
W and W' are, independently of one another, OH or COOH; preferably W=W';
p and q are, independently of one another, equal to 0 or 1;
R and R' are, independently of one another, a carbon, notably hydrocarbon, divalent radical, saturated or unsaturated, or even aromatic, linear, branched and/or cyclic; containing 1 to 12 carbon atoms, notably 2 to 8 carbon atoms, and optionally having in addition 1 or more heteroatoms selected from O, S and N, notably O (ether);
notably R and/or R' can be of formula $—(CH_2)_a—$ with a=1-12, and notably methylene, ethylene, propylene, phenylene;
or alternatively of formula $—[(CH_2)_xO]_z—$ with x=1, 2 or 3 and z=1-10; in particular x=2 or 3 and z=1-4; and preferably x=3 and z=1;
R1 to R6 are, independently of one another, a linear, branched and/or cyclic, saturated or unsaturated or even aromatic, carbon radical; containing 1 to 20 carbon atoms, notably 2 to 12 carbon atoms; preferably, R1 to R6 are saturated or alternatively aromatic, and can notably be selected from the alkyl radicals, in particular the methyl, ethyl, propyl, isopropyl, butyl, pentyl, hexyl, octyl, decyl, dodecyl and octadecyl radicals, the cycloalkyl radicals, in particular the cyclohexyl radical, the aryl radicals, notably phenyl and naphthyl, the aralkyl radicals, notably benzyl and phenylethyl, as well as the tolyl and xylyl radicals;
m and n are, independently of one another, integers between 1 and 140, and are such that the weight-average molecular weight (Mw) of the silicone is between 300 and 20 000, notably between 400 and 10 000, or even between 800 and 4000.

We may notably mention for example the α,ω-diol or α,ω-dicarboxylic polyalkylsiloxanes, and notably the α,ω-diol polydimethysiloxanes and the α,ω-dicarboxylic polydimethylsiloxanes; the α,ω-diol or α,ω-dicarboxylic polyarylsiloxanes and notably the α,ω-diol or α,ω-dicarboxylic polyphenylsiloxanes; the polyarylsiloxanes with silanol functions such as polyphenylsiloxane; the polyalkylsiloxanes with silanol functions such as polydimethylsiloxane; the polyaryl/alkylsiloxanes with silanol functions such as polyphenyl/methylsiloxane or polyphenyl/propylsiloxane.

Quite preferably, the α,ω-diol polydimethylsiloxanes of weight-average molecular weight (Mw) between 400 and 10 000, or even between 500 and 5000, and notably between 800 and 4000, will be used.

When present, said silicone can preferably represent 0.1 to 15 wt. %, notably 1 to 10 wt. %, or even 2 to 8 wt. %, of the weight of the polycondensate.

In a preferred embodiment of the invention, the aromatic monocarboxylic acid is present in a molar amount less than or equal to that of the non-aromatic monocarboxylic acid; notably the ratio of the number of moles of aromatic monocarboxylic acid to the number of moles of non-aromatic monocarboxylic acid is preferably between 0.08 and 0.70, notably between 0.10 and 0.60, in particular between 0.12 and 0.40.

It was found that this makes it possible to obtain a polymer that is advantageously soluble in the oily media generally used for formulating cosmetic compositions such as lipsticks or foundations; moreover, the film obtained has suitable stiffness and flexibility for its use in this type of formulation, while having the desired gloss and durability of the gloss.

Preferably, the polycondensate according to the invention can be obtained by reaction:

of at least one polyol selected from, alone or mixed, 1,2,6-hexanetriol, trimethylolethane, trimethylolpropane, glycerol; pentaerythritol, erythritol, diglycerol, ditrimethylolpropane; xylitol, sorbitol, mannitol, dipentaerythritol and/or triglycerol;

present preferably in an amount from 10 to 30 wt. %, notably 12 to 25 wt. %, and better still 14 to 22 wt. %, relative to the total weight of the final polycondensate;

of at least one non-aromatic monocarboxylic acid selected from, alone or mixed, caproic acid, caprylic acid, isoheptanoic acid, 4-ethylpentanoic acid, 2-ethylhexanoic acid, 4,5-dimethylhexanoic acid, 2-heptylheptanoic acid, 3,5,5-trimethylhexanoic acid, octanoic acid, isooctanoic acid, nonanoic acid, decanoic acid, isononanoic acid, lauric acid, tridecanoic acid, myristic acid, palmitic acid, stearic acid, isostearic acid, arachidic acid, behenic acid, cerotic (hexacosanoic) acid; cyclopentanecarboxylic acid, cycloopentaneacetic acid, 3-cyclopentylpropionic acid, cyclohexanecarboxylic acid, cyclohexylacetic acid, 4-cyclohexylbutyric acid;

present preferably in an amount from 30 to 80 wt. %, notably 40 to 75 wt. %, and better still 45 to 70 wt. %, relative to the total weight of the final polycondensate;

of at least one aromatic monocarboxylic acid selected from, alone or mixed, benzoic acid, o-toluic acid, m-toluic acid, p-toluic acid, 1-naphthoic acid, 2-naphthoic acid, 4-tert-butyl-benzoic acid, 1-methyl-2-naphthoic acid, 2-isopropyl-1-naphthoic acid;

present preferably in an amount from 0.1 to 10 wt. %, notably 1 to 9.5 wt. %, or even 1.5 to 8 wt. %, relative to the total weight of the final polycondensate; and of at least one polycarboxylic acid or one of its anhydrides, selected from, alone or mixed, decanedioic acid, dodecanedioic acid, cyclopropanedicarboxylic acid, cyclohexanedicarboxylic acid, cyclobutanedicarboxylic acid, naphthalene-1,4-dicarboxylic acid, naphthalene-2,3-dicarboxylic acid, naphthalene-2,6-dicarboxylic acid, suberic acid, oxalic acid, malonic acid, succinic acid, phthalic acid, terephthalic acid, isophthalic acid, pimelic acid, sebacic acid, azelaic acid, glutaric acid, adipic acid, fumaric acid, maleic acid; cyclohexanetricarboxylic acid, trimellitic acid, 1,2,3-benzenetricarboxylic acid, 1,3,5-benzenetricarboxylic acid; butanetetracarboxylic acid, pyromellitic acid, phthalic anhydride, trimellitic anhydride, maleic anhydride and succinic anhydride;

present preferably in an amount from 5 to 40 wt. %, notably 10 to 30 wt. %, and better still 14 to 25 wt. %, relative to the total weight of the final polycondensate.

Preferably, the polycondensate according to the invention can be obtained by reaction:

of at least one polyol selected from, alone or mixed, glycerol, pentaerythritol, sorbitol and mixtures thereof, and better still pentaerythritol alone; present in an amount from 10 to 30 wt. %, notably 12 to 25 wt. %, and better still 14 to 22 wt. %, relative to the total weight of the final polycondensate;

of at least one non-aromatic monocarboxylic acid selected from, alone or mixed, 2-ethylhexanoic acid, isooctanoic acid, lauric acid, palmitic acid, isostearic acid, isononanoic acid, stearic acid, behenic acid, and mixtures thereof, and better still isostearic acid alone or stearic acid alone;

present in an amount from 30 to 80 wt. %, notably 40 to 75 wt. %, and better still 45 to 70 wt. %, relative to the total weight of the final polycondensate;

of at least one aromatic monocarboxylic acid selected from, alone or mixed, benzoic acid, o-toluic acid, m-toluic acid, 1-naphthoic acid, and better still benzoic acid alone; present in an amount from 0.1 to 10 wt. %, notably 1 to 9.5 wt. %, or even 1.5 to 8 wt. % relative to the total weight of the final polycondensate; and of at least one polycarboxylic acid or one of its anhydrides, selected from, alone or mixed, phthalic anhydride and isophthalic acid, and better still isophthalic acid alone; present in an amount from 5 to 40 wt. %, notably 10 to 30 wt. %, and better still 14 to 25 wt. %, relative to the total weight of the final polycondensate.

Preferably, the polycondensate according to the invention has:

an acid number, expressed in mg of potassium hydroxide per g of polycondensate, greater than or equal to 1; notably between 2 and 30, and better still between 2.5 and 15; and/or a hydroxyl number, expressed in mg of potassium hydroxide per g of polycondensate, greater than or equal to 40; notably between 40 and 120, and better still between 45 and 80.

These acid and hydroxyl numbers can easily be determined by a person skilled in the art by the usual analytical methods.

Preferably, the polycondensate according to the invention exhibits a weight-average molecular weight (Mw) of between 1500 and 300 000, or even between 2000 and 200 000, and notably between 3000 and 100 000.

The average molecular weight can be determined by gel permeation chromatography or by light scattering, depending on the solubility of the polymer under consideration.

Preferably, the polycondensate according to the invention has a viscosity, measured at 110° C., between 20 and 4000 mPa·s, notably between 30 and 3500 mPa·s, or even between 40 and 3000 mPa·s and better still between 50 and 2500 mPa·s. This viscosity is measured in the manner described before the examples.

Moreover, the polycondensate is advantageously soluble in the oily cosmetic media usually employed, and notably in vegetable oils, alkanes, fatty esters, fatty alcohols, silicone oils, and more particularly in media comprising isododecane, Parleam, isononyl isononanoate, octyldodecanol, phenyl trimethicone, $C_{12}$-$C_{15}$ alkyl benzoate and/or D5 (decamethylcyclopentasiloxane).

By soluble, we mean that the polymer forms a clear solution in at least one solvent selected from isododecane, Parleam, isononyl isononanoate, octyldodecanol and $C_{12}$-$C_{15}$ alkyl benzoate, at the rate of at least 50 wt. %, at 70° C. Some compounds even exhibit a solubility which is particularly advantageous in some fields of use, namely a solubility in at least one of the abovementioned solvents, at the rate of at least 50 wt. %, at 25° C.

The polycondensate according to the invention can be prepared by the methods of esterification/polycondensation usually employed by a person skilled in the art. By way of illustration, a general method of preparation comprises:

mixing the polyol and the aromatic and non-aromatic monocarboxylic acids, heating the mixture under an inert atmosphere, firstly up to the melting point (generally 100-130° C.) and then at a temperature between 150 and 220° C. until the monocarboxylic acids have been consumed completely (achieved when the acid number is less than or equal to 1), preferably distilling the water as it forms, then optionally cooling the mixture to a temperature between 90 and 150° C., adding the polycarboxylic acid and/or the cyclic anhydride, and optionally the silicone with hydroxyl or carboxyl functions, in one go or in steps, then heating again to a temperature less than or equal to 220° C., notably between 170 and 220° C., preferably continuing to remove the water that forms, until the required characteristics are obtained in terms of acid number, viscosity, hydroxyl number and solubility.

It is possible to add conventional esterification catalysts, e.g. of the sulphonic acid type (notably at a concentration by weight between 1 and 10%) or of the titanate type (notably at a concentration by weight between 5 and 100 ppm).

It is also possible to carry out the reaction, completely or partially, in an inert solvent such as xylene and/or under reduced pressure, to facilitate elimination of the water.

Advantageously, neither catalyst nor solvent is used.

Said method of preparation can in addition comprise a stage of addition of at least one antioxidant to the reaction mixture, notably at a concentration by weight between 0.01 and 1%, relative to the total weight of monomers, in order to limit any degradation connected with prolonged heating.

The antioxidant can be of primary type or of secondary type, and can be selected from hindered phenols, secondary aromatic amines, organophosphorus compounds, sulphur compounds, lactones, acrylated bisphenols; and mixtures thereof.

Among the antioxidants that are particularly preferred, we may notably mention BHT, BHA, TBHQ, 1,3,5-trimethyl-2, 4,6-tris(3,5-di-tert-butyl-4-hydroxybenzyl)-benzene, octadecyl-3,5-di-tert-butyl-4-hydroxycinnamate, tetrakis-methylene-3-(3,5-di-tert-butyl-4-hydroxyphenyl)propionate methane, octadecyl-3-(3,5-di-tert-butyl-4-hydroxyphenyl) propionate, 2,5-di-tert-butyl hydroquinone, 2,2-methyl-bis-(4-methyl-6-tert-butyl phenol), 2,2-methylene-bis-(4-ethyl-6-tert-butyl phenol), 4,4-butylidene-bis(6-tert-butyl-m-cresol), N,N-hexamethylene bis(3,5-di-tert-butyl-4-hydroxyhydro-cinnamamide), pentaerythritol tetrakis(3-(3, 5-di-tert-butyl-4-hydroxyphenyl)propionate) notably that marketed by CIBA under the name IRGANOX 1010; octadecyl 3-(3,5-di-tert-butyl-4-hydroxyphenyl)propionate notably that marketed by CIBA under the name IRGANOX 1076; 1,3,5-tris(3,5-di-tert-butyl-4-hydroxybenzyl)-1,3,5-triazine-2,4,6(1H,3H,5H)trione notably that marketed by Mayzo of Norcross, Ga under the name BNX 3114; di(stearyl)pentaerythritol diphosphite, tris(2,4-ditert-butyl phenyl)phosphite notably that marketed by CIBA under the name IRGAFOS 168; dilauryl thiodipropionate notably that marketed by CIBA under the name IRGANOX PS800; bis(2,4-di-tert-butyl)pentaerythritol diphosphite notably that marketed by CIBA under the name IRGAFOS 126; bis(2,4-bis) [2-phenylpropan-2-yl]phenyl)pentaerythritol diphosphite, triphenylphosphite, (2,4-di-tert-butylphenyl)pentaerythritol diphosphite notably that marketed by GE Specialty Chemicals under the name ULTRANOX 626; tris(nonylphenyl) phosphite notably that marketed by CIBA under the name IRGAFOS TNPP; 1:1 mixture of N,N-hexamethylenebis(3, 5-di-tert-butyl-4-hydroxy-hydro-cinnamamide) and of tris(2, 4-di-tert-butylphenyl)-phosphate notably that marketed by CIBA under the name Irganox B 1171; tetrakis(2,4-di-tert-butylphenyl)-phosphite notably that marketed by CIBA under the name IRGAFOS P-EPQ; distearylthiodipropionate notably that marketed by CIBA under the name IRGANOX PS802; 2,4-bis(octylthiomethyl)o-cresol notably that marketed by CIBA under the name IRGANOX 1520; 4,6-bis (dodecylthiomethyl)o-cresol notably that marketed by CIBA under the name IRGANOX 1726.

The polycondensates according to the invention can be used very advantageously in a composition, notably cosmetic or pharmaceutical, which in addition comprises a physiologically, notably cosmetically or pharmaceutically, acceptable medium, i.e. a medium compatible with cutaneous tissues such as the skin of the face or of the body, and keratinous materials such as the hair, eyelashes, eyebrows and nails.

The amount of polycondensate in the compositions depends of course on the type of composition and on the properties required, and can vary over a very wide range, generally between 0.1 and 70 wt. %, preferably between 1 and 50 wt. %, notably between 10 and 45 wt. %, or even between 20 and 40 wt. %, and most preferably between 25 and 35 wt. %, relative to the weight of the final cosmetic or pharmaceutical composition.

The composition can then include, depending on the application envisaged, the constituents that are usual for this type of composition.

The composition according to the invention can advantageously comprise an oily liquid phase, which can be a solvent of the polymers according to the invention, and which can include at least one compound selected from oils and/or solvents of mineral, animal, vegetable or synthetic origin, carbon-containing, hydrocarbon-containing, fluorinated and/or siliconized, volatile or non-volatile, alone or mixed provided they form a homogeneous, stable mixture and are compatible with the intended use.

By "volatile", we mean in the sense of the invention, any compound that will evaporate when in contact with keratinous materials, or the lips, in less than an hour, at room temperature (25° C.) and atmospheric pressure (1 atm). Notably, this volatile compound has a non-zero vapour pressure, at room temperature and atmospheric pressure, notably in the range from 0.13 Pa to 40 000 Pa ($10^{-3}$ at 300 mmHg), in particular in the range from 1.3 Pa to 13 000 Pa (0.01 to 100 mmHg), and more particularly in the range from 1.3 Pa to 1300 Pa (0.01 to 10 mmHg). Conversely, by "non-volatile", we mean a compound that remains on keratinous materials or on the lips, at room temperature and atmospheric pressure, for at least one hour and notably has a vapour pressure below $10^{-3}$ mmHg (0.13 Pa).

Preferably, the physiologically acceptable medium of the composition according to the invention can contain, in an oily liquid phase, at least one oil and/or solvent which can be selected from, alone or mixed:

1/esters of monocarboxylic acids with monoalcohols and polyalcohols; advantageously, said ester is a $C_{12}$-$C_{15}$ alkyl benzoate or corresponds to the following formula:

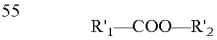

where:

$R'_1$ represents a linear or branched alkyl radical with 1 to 40 carbon atoms, preferably with 7 to 19 carbon atoms, optionally having one or more ethylenic double bonds, optionally substituted and whose hydrocarbon chain can be interrupted by one or more heteroatoms selected from N and O and/or one or more carbonyl functions, and $R'_2$ represents a linear or branched alkyl radical with 1 to 40 carbon atoms, preferably with 3 to 30 carbon atoms and more preferably with 3 to 20 carbon atoms, optionally having one or more ethylenic double bonds, optionally substituted and whose hydrocarbon chain can be interrupted by one or more heteroatoms selected from N and O and/or one or more carbonyl functions.

By "optionally substituted", we mean that $R'_1$ and/or $R'_2$ can have one or more substituents selected, for example, from groups comprising one or more heteroatoms selected from O and/or N, such as amino, amine, alkoxy, hydroxyl.

Examples of the groups $R'_1$ are those derived from the, preferably higher, fatty acids selected from the group comprising acetic, propionic, butyric, caproic, caprylic, pelargonic, capric, undecanoic, lauric, myristic, palmitic, stearic, isostearic, arachidic, behenic, oleic, linolenic, linoleic, oleostearic, arachidonic, erucic acids and mixtures thereof. Preferably, $R'_1$ is an unsaturated branched alkyl group with 4 to 14 carbon atoms, preferably with 8 to 10 carbon atoms and $R_2$ is an unsaturated branched alkyl group with 5 to 15 carbon atoms, preferably with 9 to 11 carbon atoms.

In particular we may mention, preferably, the $C_8$-$C_{48}$ esters, optionally incorporating, in their hydrocarbon chain one, or more heteroatoms selected from N and O and/or one or more carbonyl functions; and more particularly purcellin oil (cetostearyl octanoate), isononyl isononanoate, isopropyl myristate, isopropyl palmitate, ethyl-2-hexyl palmitate, octyl-2-dodecyl stearate, octyl-2-dodecyl erucate, isostearyl isostearate, benzoate of $C_{12}$ to $C_{15}$ alcohol, hexyl laurate, diisopropyl adipate; and the heptanoates, octanoates, decanoates or ricinoleates of alcohols or of polyalcohols, for example of fatty alcohols such as propylene glycol dioctanoate, as well as N-lauroyl isopropyl sarcosinate (notably Eldew-205SL from Ajinomoto); hydroxylated esters such as isostearyl lactate, di-isostearyl malate; and esters of pentaerythritol; $C_8$-$C_{16}$ branched esters, notably isohexyl neopentanoate.

2/hydrocarbon vegetable oils with high content of triglycerides, comprising esters of fatty acids and of glycerol, with the fatty acids having chain lengths varying from $C_4$ to $C_{24}$, and the latter can be linear or branched, saturated or unsaturated; these oils are notably wheat germ oil, maize oil, sunflower oil, shea oil, castor oil, sweet almond oil, macadamia oil, apricot oil, soya oil, colza oil, cottonseed oil, lucerne oil, poppy seed oil, Chinese okra oil, sesame oil, cucurbit oil, avocado oil, hazelnut oil, grape seed or blackcurrant oil, evening primrose oil, millet oil, barley oil, quinoa oil, olive oil, rye oil, safflower oil, candlenut oil, passionflower oil, musk rose oil, jojoba oil, palm oil, calophyllum oil; or the triglycerides of caprylic/capric acids such as those sold by the company Stearinerie Dubois or those sold under the names "Miglyol 810®", "812®" and "818®" by the company Dynamit Nobel.

3/$C_6$-$C_{32}$, notably $C_{12}$-$C_{26}$, alcohols, and notably monoalcohols, such as oleic alcohol, linoleic alcohol, linolenic alcohol, isostearyl alcohol, 2-hexyldecanol, 2-butyloctanol, 2-undecylpentadecanol and octyldodecanol;

4/hydrocarbon oils, linear or branched, volatile or non-volatile, of synthetic or mineral origin, which can be selected from the hydrocarbon oils having from 5 to 100 carbon atoms, and notably petroleum jelly, polydecenes, hydrogenated polyisobutenes such as Parleam, squalane, perhydrosqualene and mixtures thereof.

We may mention more particularly the linear, branched and/or cyclic $C_5$-$C_{48}$ alkanes, and preferably the $C_8$-$C_{16}$ branched alkanes such as the $C_8$-$C_{16}$ isoalkanes of petroleum origin (also called isoparaffins); notably decane, heptane, dodecane, cyclohexane; as well as isododecane, isodecane, isohexadecane.

5/the volatile or non-volatile silicone oils.

As volatile silicone oils, we may mention the volatile linear or cyclic silicone oils, notably those having a viscosity below 8 centistokes, and notably having from 2 to 10 silicon atoms, these silicones optionally comprising alkyl or alkoxy groups with from 1 to 22 carbon atoms; and in particular octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane, methylhexyldimethylsiloxane, and mixtures thereof.

The non-volatile silicone oils that can be used according to the invention can be the polydimethylsiloxanes (PDMS), the polydimethylsiloxanes having alkyl or alkoxy groups, pendent and/or at the end of the silicone chain, groups each with 2 to 24 carbon atoms, the phenylated silicones such as phenyltrimethicones, phenyldimethicones, phenyltrimethylsiloxydiphenylsiloxanes, diphenyldimethicones, diphenylmethyldiphenyltrisiloxanes, 2-phenylethyl trimethylsiloxysilicates.

Preferably, the physiologically acceptable medium of the composition according to the invention comprises, in an oily liquid phase, at least one oil and/or solvent selected from, alone or mixed, isododecane, Parleam, isononyl isononanoate, octyldodecanol, phenyl trimethicone, $C_{12}$-$C_{15}$ alkyl benzoates and/or D5 (decamethylcyclopentasiloxane).

The oily liquid phase can moreover contain additional oils and/or solvents, which can for example be selected from, alone or mixed:

fluorinated oils such as perfluoropolyethers, perfluoroalkanes such as perfluorodecalin, perfluorodamantanes, the monoesters, diesters and triesters of perfluoroalkylphosphates and fluorinated ester oils;

oils of animal origin;

$C_6$ to $C_{40}$ ethers, notably $C_{10}$-$C_{40}$; propylene glycol ethers that are liquid at room temperature such as propylene glycol monomethylether, propylene glycol monomethylether acetate, mono n-butyl ether of dipropylene glycol;

$C_8$-$C_{32}$ fatty acids, such as oleic acid, linoleic acid, linolenic acid and mixtures thereof;

bifunctional oils, containing two functions selected from ester and/or amide and having from 6 to 30 carbon atoms, notably 8 to 28 carbon atoms, preferably 10 to 24 carbons, and 4 heteroatoms selected from O and N; the amide and ester functions preferably being in the chain;

ketones that are liquid at room temperature (25° C.), such as methyl ethyl ketone, methyl isobutyl ketone, diisobutyl ketone, isophorone, cyclohexanone, acetone;

aldehydes that are liquid at room temperature, such as benzaldehyde, acetaldehyde.

The oily liquid phase can represent 1 to 90 wt. % of the composition, notably from 5 to 75 wt. %, in particular from 10 to 60 wt. %, or even from 25 to 55 wt. %, of the total weight of the composition.

The composition according to the invention can advantageously include a thickening agent which can in particular be selected from:

silicas, notably hydrophobic, such as those described in document EP-A-898960, and for example marketed under the references "AEROSIL R812®" by the company Degussa, "CAB-O-SIL TS-530®", "CAB-O-SIL TS-610®", "CAB-O-SIL TS-720®" by the company Cabot, "AEROSIL R972®", "AEROSIL R974®" by the company Degussa;

clays, such as montmorillonite, modified clays such as the bentones for example, stearalkonium hectorite, stearalkonium bentonite;

polysaccharide alkyl ethers (notably with the alkyl group having from 1 to 24 carbon atoms, preferably 1 to 10, more preferably 1 to 6, and more especially 1 to 3) such as those described in document EP-A-898958.

The amount of thickening agent in the composition according to the invention can range from 0.05 to 40 wt. %, relative to the total weight of the composition, preferably from 0.5 to 20% and more preferably from 1 to 15 wt. %.

The composition according to the invention can also include at least one wax of vegetable, animal, mineral or synthetic origin, or even siliconized.

We may mention in particular, alone or mixed, the hydrocarbon waxes such as beeswax; carnauba wax, candelilla wax, ouricury wax, Japan wax, waxes from cork fibre or sugar cane; paraffin wax, lignite wax; microcrystalline waxes; lanolin wax; montane wax; ozokerites; polyethylene waxes; waxes obtained by Fischer-Tropsch synthesis; hydrogenated oils, fatty esters and glycerides that are solid at 25° C. It is also possible to use silicone waxes, among which we may mention the alkyls, alkoxyls and/or esters of polymethylsiloxane.

The amount of wax in the composition according to the invention can range from 0.1 to 70 wt. %, relative to the total weight of the composition, preferably from 1 to 40 wt. %, and more preferably from 5 to 30 wt. %.

The composition according to the invention can also include one or more colorants selected from pulverulent compounds such as pigments, fillers, nacres and flakes, and/or fat-soluble or water-soluble colorants.

The colorants, notably pulverulent, can be present in the composition at a content from, for example, 0.01 to 50 wt. %, relative to the weight of the composition, preferably from 0.1 to 40 wt. %, or even from 1 to 30 wt. %.

By pigments, we mean particles of any shape, white or coloured, mineral or organic, insoluble in the physiological medium, and intended to colour the composition.

By nacres, we mean iridescent particles of any shape, notably produced in the shell of certain molluscs, or alternatively synthesized.

The pigments can be white or coloured, mineral and/or organic, interferential or non-interferential. We may mention, among the mineral pigments, titanium dioxide, optionally surface-treated, oxides of zirconium or of cerium, as well as oxides of iron or of chromium, manganese violet, ultramarine, chromium hydrate and ferric blue. Among organic pigments, we may mention carbon black, D & C pigments, and lakes based on carmine, barium, strontium, calcium, aluminium.

The nacreous pigments can be selected from white nacreous pigments such as mica coated with titanium, or with bismuth oxychloride, coloured nacreous pigments such as titanium mica with iron oxides, titanium mica notably with ferric blue or chromium oxide, titanium mica with an organic pigment of the type mentioned above as well as the nacreous pigments based on bismuth oxychloride.

The fillers can be mineral or organic, lamellar or spherical. We may mention talc, mica, silica, kaolin, powders of nylon and polyethylene, of poly-β-alanine and polyethylene, Teflon, lauroyl lysine, starch, boron nitride, powders of tetrafluoroethylene polymers, hollow microspheres such as Expancel (Nobel Industrie), polytrap (Dow Corning) and silicone resin microspheres (Tospearls from Toshiba, for example), precipitated calcium carbonate, magnesium carbonate and hydrocarbonate, hydroxyapatite, hollow silica microspheres (SILICA BEADS from MAPRECOS), glass or ceramic microcapsules, metallic soaps derived from organic carboxylic acids having from 8 to 22 carbon atoms, preferably 12 to 18 carbon atoms, for example zinc stearate, magnesium stearate or lithium stearate, zinc laurate, magnesium myristate.

Fat-soluble colorants are for example Sudan red, DC Red 17, DC Green 6, β-carotene, soya oil, Sudan brown, DC Yellow 11, DC Violet 2, DC orange 5, quinoline yellow. They can represent 0.01 to 20% of the weight of the composition and preferably 0.1 to 6%.

Water-soluble colorants are for example beetroot juice, methylene blue and can represent 0.01 to 6% of the total weight of the composition.

The composition can further include other ingredients commonly used in cosmetic compositions. Said ingredients can be selected from antioxidants, perfumes, essential oils, preservatives, cosmetic actives, hydrating agents, vitamins, ceramides, sun filters, surfactants, spreading agents, wetting agents, dispersants, antifoaming agents, neutralizing agents, stabilizers, polymers and notably fat-soluble film-forming polymers, and mixtures thereof.

Of course, a person skilled in the art will carefully select any said additional compound or compounds, and/or their quantity, in such a way that the advantageous properties of the composition for use according to the invention are not, or substantially not, adversely affected by the addition envisaged.

The compositions according to the invention can be in any form that is acceptable and usual for a cosmetic or pharmaceutical composition.

They can therefore be in the form of a suspension, a dispersion notably of oil in water based on vesicles; an organic or oily solution optionally thickened or even gelled; an oil-in-water, water-in-oil, or multiple emulsion; a gel or a mousse; an oily or emulsified gel; a dispersion of vesicles, notably lipid vesicles; a two-phase or multiphase lotion; a spray; a lotion, a cream, an ointment, a soft paste, an unguent, a poured or cast solid and notably as a stick or in a dish, or a compacted solid.

A person skilled in the art will be able to choose the appropriate galenical form, as well as its method of preparation, on the basis of his general knowledge, taking into account on the one hand the nature of the constituents used, notably their solubility in the substrate, and on the other hand the application envisaged for the composition.

As the compositions according to the invention display a gloss and a durability of said gloss that are improved relative to the state of the art, they can be used for the care or the make-up of keratinous materials such as the hair, the skin, the eyelashes, the eyebrows, the nails, the lips, the scalp and more particularly for make-up of the lips, eyelashes and/or face.

They can therefore be in the form of a product for care and/or make-up of the skin of the body or of the face, of the lips, of the eyelashes, of the eyebrows, of the hair, of the scalp or of the nails; a suntan product or self-tanning product; a hair-care product notably for the colouring, conditioning and/or care of the hair; they are advantageously in the form of mascara, lipstick, lip gloss, blusher, eye shadow, foundation.

The invention further relates to a method of cosmetic treatment of keratinous materials, notably of the skin of the body or of the face, of the lips, of the nails, of the hair and/or of the eyelashes, comprising the application of a cosmetic composition as defined previously on said materials.

This method according to the invention notably provides care or make-up of the lips, by application of a composition of lipstick or of lip gloss according to the invention.

The invention is illustrated in more detail in the following examples.

Method of Measurement of Viscosity

The viscosity at 80° C. or at 110° C. of the polymer is measured by means of a cone-plate viscosimeter of the BROOKFIELD CAP 1000+ type.

The appropriate cone-plate is determined by a person skilled in the art, on the basis of his knowledge; notably:
between 50 and 500 mPa·s, a cone 02 can be used
between 500 and 1000 mPa·s: cone 03
between 1000 and 4000 mPa·s: cone 05
between 4000 and 10 000 mPa·s: cone 06.

EXAMPLE 1

Synthesis of Pentaerythrityl Benzoate/Isophthalate/Isostearate/PDMS

A reactor equipped with a mechanical stirrer, an argon feed pipe and a distillation system is charged with 32 g of benzoic acid, 504 g of isostearic acid and 136 g of pentaerythritol, then it is heated gradually, under a gentle stream of argon, at 110-130° C. to obtain a homogeneous solution. Then the temperature is raised gradually to 180° C., maintaining this temperature for about 2 hours. The temperature is raised further to 220° C. and is held at this level until an acid number less than or equal to 1 is obtained, which takes about 9 hours. After cooling to a temperature between 100 and 130° C., 144 g of isophthalic acid and 80 g of silicone α,ω-diol X22-160AS from Shin-Etsu are added, and it is again heated gradually to 220° C. for about 15 hours.

750 g of pentaerythrityl benzoate/isophthalate/isostearate/PDMS polycondensate is obtained in the form of an oil.
The polycondensate has the following characteristics:
soluble at 50 wt. %, at 25° C., in Parleam
Acid number=12.8
Hydroxyl number=42
Mw=11 700
$\eta_{80°\,C.}$=798 mPa·s
$\eta_{110°\,C.}$=190 mPa·s
ratio of the number of moles of aromatic monocarboxylic acid to the number of moles of non-aromatic monocarboxylic acid: 0.15.

EXAMPLE 2

Synthesis of Pentaerythrityl Benzoate/Isophthalate/Isostearate

A reactor equipped with a mechanical stirrer, an argon feed pipe and a distillation system is charged with 20 g of benzoic acid, 280 g of isostearic acid and 100 g of pentaerythritol, then it is heated gradually, under a gentle stream of argon, at 110-130° C. to obtain a homogeneous solution. Then the temperature is raised gradually to 180° C., maintaining this temperature for about 2 hours. The temperature is raised further to 220° C. and is held at this level until an acid number less than or equal to 1 is obtained, which takes about 11 hours. After cooling to a temperature between 100 and 130° C., 100 g of isophthalic acid is added, and it is again heated gradually to 220° C. for about 11 hours.

405 g of pentaerythrityl benzoate/isophthalate/isostearate polycondensate is obtained in the form of a very thick oil.
The polycondensate has the following characteristics:
soluble at 50 wt. %, at 25° C., in Parleam
Acid number=3.7
Hydroxyl number=72
Mw=59 400
$\eta_{110°\,C.}$=1510 mPa·s
ratio of the number of moles of aromatic monocarboxylic acid to the number of moles of non-aromatic monocarboxylic acid: 0.16.

EXAMPLE 3

Synthesis of Pentaerythrityl Benzoate/Isophthalate/Isostearate

A reactor equipped with a mechanical stirrer, an argon feed pipe and a distillation system is charged with 35 g of benzoic acid, 270 g of isostearic acid and 80 g of pentaerythritol, then it is heated gradually, under a gentle stream of argon, at 110-130° C. to obtain a homogeneous solution. Then the temperature is raised gradually to 180° C., maintaining this temperature for about 2 hours. The temperature is raised further to 220° C. and is held at this level until an acid number less than or equal to 1 is obtained, which takes about 11 hours. After cooling to a temperature between 100 and 130° C., 65 g of isophthalic acid is added, and it is again heated gradually to 220° C. for about 5 hours.

380 g of pentaerythrityl benzoate/isophthalate/isostearate polycondensate is obtained in the form of an oil.
The polycondensate has the following characteristics:
soluble at 50 wt. %, at 25° C., in Parleam
Acid number=5.5
Hydroxyl number=103
Mw=7200
$\eta_{80°\,C.}$=700 mPa·s
ratio of the number of moles of aromatic monocarboxylic acid to the number of moles of non-aromatic monocarboxylic acid: 0.30.

EXAMPLE 4

Synthesis of Pentaerythrityl Benzoate/Isophthalate/Isostearate/PDMS

A reactor equipped with a mechanical stirrer, an argon feed pipe and a distillation system is charged with 14 g of benzoic acid, 255 g of isostearic acid and 75 g of pentaerythritol, then it is heated gradually, under a gentle stream of argon, at 110-130° C. to obtain a homogeneous solution. Then the temperature is raised gradually to 180° C., maintaining this temperature for about 2 hours. The temperature is raised further to 220° C. and is held at this level until an acid number less than or equal to 1 is obtained, which takes about 7 hours. After cooling to a temperature between 100 and 130° C., 65 g of isophthalic acid and 38 g of silicone α,ω-dicarboxy Tegomer C—Si 2342 (Goldschmidt) are added, and it is again heated gradually to 220° C. for about 15 hours.

375 g of pentaerythrityl benzoate/isophthalate/isostearate/PDMS polycondensate is obtained in the form of a thick oil.
The polycondensate has the following characteristics:
soluble at 50 wt. %, at 25° C., in Parleam
Acid number=5.5
Hydroxyl number=110
$\eta_{80°\,C.}$=1332 mPa·s
ratio of the number of moles of aromatic monocarboxylic acid to the number of moles of non-aromatic monocarboxylic acid: 0.12.

EXAMPLE 5

Synthesis of Pentaerythrityl Benzoate/Isophthalate/Isostearate/PDMS

A reactor equipped with a mechanical stirrer, an argon feed pipe and a distillation system is charged with 16 g of benzoic acid, 252 g of isostearic acid and 68 g of pentaerythritol, then it is heated gradually, under a gentle stream of argon, at 110-130° C. to obtain a homogeneous solution. Then the temperature is raised gradually to 180° C., maintaining this temperature for about 2 hours. The temperature is raised further to 220° C. and is held at this level until an acid number less than or equal to 1 is obtained, which takes about 9 hours. After cooling to a temperature between 100 and 130° C., 40 g of isophthalic acid and 40 g of silicone α,ω-diol X22-160AS from Shin-Etsu are added, and it is again heated gradually to 220° C. for about 7 hours.

345 g of pentaerythrityl benzoate/isophthalate/isostearate/PDMS polycondensate is obtained in the form of an oil.

The polycondensate has the following characteristics:
soluble at 50 wt. %, at 25° C., in Parleam
Acid number=2.5
Hydroxyl number=63
Mw=3600
$\eta_{80° C.}$=125 mPa·s
ratio of the number of moles of aromatic monocarboxylic acid to the number of moles of non-aromatic monocarboxylic acid: 0.15.

EXAMPLE 6

Synthesis of Pentaerythrityl Benzoate/Isophthalate/Stearate

A reactor equipped with a mechanical stirrer, an argon feed pipe and a distillation system is charged with 10 g of benzoic acid, 370 g of stearic acid and 95 g of pentaerythritol, then it is heated gradually, under a gentle stream of argon, at 110-130° C. to obtain a homogeneous solution. Then the temperature is raised gradually to 180° C., and maintained for about 2 hours. The temperature is raised further to 220° C. and is held at this level until an acid number less than or equal to 1 is obtained, which takes about 11 hours. After cooling to a temperature between 100 and 130° C., 90 g of isophthalic acid is added, and it is again heated gradually to 220° C. for about 11 hours.

430 g of pentaerythrityl benzoate/isophthalate/stearate polycondensate is obtained in the form of a very thick oil.

The polycondensate has the following characteristics:
soluble at 50 wt. %, at 70° C., in Parleam
Acid number=10.8
Mw=8800
$\eta_{80° C.}$=360 mPa·s

EXAMPLE 7

The preparation is carried out in a way similar to the preceding examples of the following polycondensates (the % are by weight):

| | Polyol (% and nature) | Aromatic acid (% and nature) | Polycarboxylic acid or anhydride (% and nature) | Nonaromatic acid (% and nature) | Solubility* |
|---|---|---|---|---|---|
| Example A | 21.6 pentaerythritol | 3.9 benzoic | 19.5 isophthalic acid | 27.5% isostearic + 27.5% isononanoic | at 25° C. |
| Example B | 16.8 pentaerythritol | 1.8 benzoic | 15.9 isophthalic acid | 65.5 behenic | at 70° C. |
| Example C | 20 pentaerythritol | 4 tert-butylbenzoic | 20 isophthalic acid | 56 isostearic | at 25° C. |
| Example D | 17.4 glycerol | 8.6 benzoic | 16 isophthalic acid | 58 isostearic | at 25° C. |
| Example E | 20.7 glycerol | 8.5 tert-butyl-benzoic | 15.9 adipic acid | 54.9 isononanoic | at 25° C. |
| Example F | 25.5 diglycerol | 2 benzoic | 13.7 isophthalic acid | 58.8 isononanoic | at 25° C. |
| Example G | 28 ditrimethylol-propane | 2 1-naphthoic | 14 isophthalic acid | 56 isostearic | at 25° C. |
| Example H | 25.2 trimethylol-propane | 5.8 benzoic | 12.6 isophthalic acid | 56.3 isononanoic | at 25° C. |
| Example I | 25 trimethylol-propane | 2.1 m-toluic | 14.6 phthalic anhydride | 58.3 isostearic | at 25° C. |
| Example J | 21.9 erythritol | 6.3 tert-butyl-benzoic | 13.5 sebacic acid | 58.3 isooctanoic | at 25° C. |
| Example K | 20.4 dipenta-erythritol | 6.1 benzoic | 20.4 Pripol 1009** | 53.1 isostearic | at 25° C. |
| Example L | 28 ditrimethylol-propane | 2 1-naphthoic | 14 isophthalic acid | 40% isostearic + 16% 2-ethyl-hexanoic | at 25° C. |

-continued

|  | Polyol (% and nature) | Aromatic acid (% and nature) | Polycarboxylic acid or anhydride (% and nature) | Nonaromatic acid (% and nature) | Solubility* |
|---|---|---|---|---|---|
| Example M | 21.3 pentaerythritol | 6.4 benzoic | 17 succinic acid | 27.7% nonanoic + 27.6% isoheptanoic | at 25° C. |
| Example N | 17.4 glycerol | 8.6 benzoic | 16 isophthalic acid | 58 stearic | at 70° C. |
| Example O | 25.5 diglycerol | 2 benzoic | 13.7 isophthalic acid | 58.8 myristic | at 70° C. |
| Example P | 25.5 diglycerol | 3.9 benzoic | 15.7 sebacic acid | 54.9 lauric | at 70° C. |
| Example Q | 20.4 dipenta-erythritol | 6.1 benzoic | 20.4 Pripol 1009** | 53.1 behenic | at 70° C. |
| Example R | 25.2 trimethylol-propane | 5.8 benzoic | 12.6 isophthalic acid | 31.1% stearic + 25.3% behenic | at 70° C. |

*"at 25° C." indicates that the polymer is soluble at 50 wt. %, at 25° C., in Parleam; "at 70° C." indicates that the polymer is soluble at 50 wt. %, at 70° C., in Parleam
**Pripol 1009 from Uniqema: oleic acid dimer

EXAMPLE 8

A gloss having the following composition was prepared:

| | |
|---|---|
| polycondensate of Example 1 | 29 g |
| polybutene | 34 g |
| isononyl isononanoate | 4 g |
| octyldodecanol | 10 g |
| silica (Aerosil R972) | 5 g |
| tridecyl trimellitate | qsf 100 g |

After application on the lips, a glossy film is obtained, which remains glossy for at least 2 hours.

EXAMPLE 9

A gloss having the following composition was prepared:

| | |
|---|---|
| polycondensate of Example 2 | 28 g |
| polybutene | 34 g |
| isononyl isononanoate | 4 g |
| octyldodecanol | 10 g |
| silica (Aerosil R972) | 5 g |
| tridecyl trimellitate | qsf 100 g |

After application on the lips, a glossy film is obtained, which remains glossy for at least 2 hours.

EXAMPLE 10

A lipstick having the following composition was prepared:

| | |
|---|---|
| polycondensate of Example 2 | 30 g |
| polyethylene wax | 11 g |
| pigments and fillers | 7 g |
| Parleam (hydrogenated isoparaffin) | qsf 100 g |

After application on the lips, a coloured, glossy film is obtained, which remains glossy for at least 2 hours.

EXAMPLE 11

A lipstick having the following composition was prepared:

| | |
|---|---|
| polycondensate of Example 6 | 10 g |
| polyethylene wax | 11 g |
| pigments and fillers | 7 g |
| Parleam (hydrogenated isoparaffin) | qsf 100 g |

After application on the lips, a coloured, glossy film is obtained, which remains glossy for at least 2 hours.

The above written description of the invention provides a manner and process of making and using it such that any person skilled in this art is enabled to make and use the same, this enablement being provided in particular for the subject matter of the appended claims, which make up a part of the original description and including a cosmetic or pharmaceutical composition comprising, in a cosmetically or pharmaceutically acceptable medium, at least one polycondensate that can be obtained by reaction:

of 10 to 30 wt. %, relative to the total weight of the polycondensate, of at least one polyol containing 3 to 6 hydroxyl groups;

of 30 to 80 wt. %, relative to the total weight of the polycondensate, of at least one saturated or unsaturated, linear, branched and/or cyclic, non-aromatic monocarboxylic acid, containing 6 to 32 carbon atoms;

of 0.1 to 10 wt. %, relative to the total weight of the polycondensate, of at least one aromatic monocarboxylic acid containing 7 to 11 carbon atoms, optionally in addition substituted with 1 to 3 saturated or unsaturated, linear, branched and/or cyclic alkyl radicals, which contain 1 to 32 carbon atoms;

of 5 to 40 wt. %, relative to the total weight of the polycondensate, of at least one polycarboxylic acid, saturated or unsaturated, or even aromatic, linear, branched and/or cyclic, containing at least 2 carboxyl groups COOH, notably 2 to 4 COOH groups; and/or a cyclic anhydride of such a polycarboxylic acid.

As used herein, the phrases "selected from the group consisting of," "chosen from," and the like include mixtures of the specified materials. Terms such as "contain(s)" and the like as used herein are open terms meaning 'including at least' unless otherwise specifically noted.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

The invention claimed is:

1. A composition comprising, in a cosmetically or pharmaceutically acceptable medium, at least one polycondensate obtained by reaction of 10 to 30 wt. %, relative to the total weight of the polycondensate, of at least one polyol which is a linear, branched or cyclic hydrocarbon, saturated or unsaturated, having 3 to 18 carbon atoms and 3 to 6 hydroxyl groups (OH), optionally having one or more ether groups;
of 30 to 80 wt. %, relative to the total weight of the polycondensate, of at least one saturated, linear, branched and/or cyclic, non-aromatic monocarboxylic acid of formula RCOOH, in which R is a saturated, linear, branched and/or cyclic hydrocarbon radical, having 5 to 31 carbon atoms;
of 0.1 to 10 wt. %, relative to the total weight of the polycondensate, of at least one aromatic monocarboxylic acid of formula R'COOH, in which R' is an aromatic hydrocarbon radical, containing 6 to 10 carbon atoms; said radical R' can optionally be substituted with 1 to 3 saturated or unsaturated, linear, branched and/or cyclic alkyl radicals, which have 1 to 32 carbon atoms; and
of 5 to 40 wt. %, relative to the total weight of the polycondensate, of at least one polycarboxylic acid, saturated or unsaturated, aromatic, linear, branched and/or cyclic, having at least 2 carboxyl groups COOH and/or a cyclic anhydride of said polycarboxylic acid, wherein the ratio of the number of moles of aromatic monocarboxylic acid to the number of moles of non-aromatic monocarboxylic acid is between 0.08 and 0.70.

2. The composition according to claim 1, wherein the polyol has 3 to 4 hydroxyl groups.

3. The composition according to claim 1, wherein the polyol is a saturated, linear or branched hydrocarbon compound having 3 to 12 carbon atoms and 3 to 6 hydroxyl groups (OH).

4. The composition according to claim 1, wherein the polyol is selected from the group consisting of 1,2,4-butanetriol, 1,2,6-hexanetriol, trimethylolethane, trimethylolpropane, glycerol, pentaerythritol, erythritol, diglycerol ditrimethylolpropane, xylitol, sorbitol, mannitol, dipentaerythritol, triglycerol, and mixtures thereof.

5. The composition according to claim 1, wherein the polyol is pentaerythritol.

6. The composition according to claim 1, wherein the at least one polyol represents 12 to 25 wt. % of the total weight of the polycondensate.

7. The composition according to claim 1, wherein the radical R is linear or branched $C_5$-$C_{31}$.

8. The composition according to claim 1, wherein the non-aromatic monocarboxylic acid is selected from the group consisting of caproic acid, caprylic acid, isoheptanoic acid, 4-ethylpentanoic acid, 2-ethylhexanoic acid, 4,5-dimethylhexanoic acid, 2-heptylheptanoic acid, 3,5,5-trimethylhexanoic acid, octanoic acid, isooctanoic acid, nonanoic acid, decanoic acid, isononanoic acid, lauric acid, tridecanoic acid, myristic acid, palmitic acid, stearic acid, isostearic acid, arachidic acid, behenic acid, cerotic (hexacosanoic) acid, cyclopentanecarboxylic acid, cyclopentaneacetic acid, 3-cyclopentylpropionic acid, cyclohexanecarboxylic acid, cyclohexylacetic acid, 4-cyclohexylbutyric acid, and mixtures thereof.

9. The composition according to claim 1, wherein the non-aromatic monocarboxylic acid is selected from the group consisting of 2-ethylhexanoic acid, isooctanoic acid, lauric acid, myristic acid, isoheptanoic acid, isononanoic acid, nonanoic acid, palmitic acid, isostearic acid, stearic acid, behenic acid, and mixtures thereof.

10. The composition according to claim 1, wherein the at least one non-aromatic monocarboxylic acid represents 40 to 75 wt. % of the total weight of the final polycondensate.

11. The composition according to claim 1, wherein the aromatic monocarboxylic acid is selected from the group consisting of benzoic acid, o-toluic acid, m-toluic acid, p-toluic acid, 1-naphthoic acid, 2-naphthoic acid, 4-tert-butyl benzoic acid, 1-methyl-2-naphthoic acid, 2-isopropyl-1-naphthoic acid and mixtures thereof.

12. The composition according to claim 1, wherein the aromatic monocarboxylic acid is selected from the group consisting of benzoic acid, 4-tert-butyl benzoic acid, o-toluic acid, m-toluic acid, 1-naphthoic acid, and mixtures thereof.

13. The composition according to claim 1, wherein the at least one aromatic monocarboxylic acid represents 0.5 to 9.95 wt. % of the total weight of the final polycondensate.

14. The composition according to claim 1, wherein the polycarboxylic acid is selected from linear, branched and/or cyclic polycarboxylic acids, saturated or unsaturated, including aromatic, containing 2 to 50 carbon atoms, said acid having at least two carboxyl groups COOH.

15. The composition according to claim 14, wherein said polycarboxylic acid is saturated, linear aliphatic, and comprises 2 to 36 carbon atoms.

16. The composition according to claim 14, wherein said polycarboxylic acid is aromatic and comprises 8 to 12 carbon atoms.

17. The composition according to claim 1, wherein the polycondensate is obtained by reaction of at least one cyclic anhydride corresponding to at least one of the following formulae:

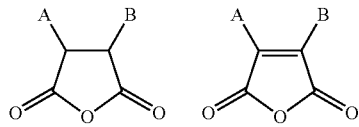

in which groups A and B are, independently of one another:
a hydrogen atom;
a carbon radical, aliphatic, saturated or unsaturated, linear, branched and/or cyclic, or alternatively aromatic; having 1 to 16 carbon atoms; or alternatively A and B taken together form a ring having a total of 5 to 7 carbon atoms, saturated or unsaturated, or aromatic.

18. The composition according to claim 17, wherein A and B represent a hydrogen atom or together form an aromatic ring having a total of 6 carbon atoms.

19. The composition according to claim 1, wherein the polycarboxylic acid or its anhydride is selected from:
   decanedioic acid, dodecanedioic acid, cyclopropanedicarboxylic acid, cyclohexanedicarboxylic acid, cyclobutanedicarboxylic acid, naphthalene-1,4-dicarboxylic acid, naphthalene-2,3-dicarboxylic acid, naphthalene-2,6-dicarboxylic acid, suberic acid, oxalic acid, malonic acid, succinic acid, phthalic acid, terephthalic acid, isophthalic acid, tetrahydrophthalic acid, hexahydrophthalic acid, pimelic acid, sebacic acid, azelaic acid, glutaric acid, adipic acid, fumaric acid, maleic acid, itaconic acid, dimers of fatty acids (notably of $C_{36}$);
   cyclohexanetricarboxylic acid, trimellitic acid, 1,2,3-benzenetricarboxylic acid, 1,3,5-benzenetricarboxylic acid;
   butanetetracarboxylic acid and pyromellitic acid; cyclic anhydrides of these acids;
   and mixtures thereof.

20. The composition according to claim 1, wherein the polycarboxylic acid or its anhydride is selected from adipic acid, phthalic anhydride and/or isophthalic acid.

21. The composition according to claim 1, wherein the polycarboxylic acid and/or its cyclic anhydride represents 10 to 30 wt. % of the total weight of the polycondensate.

22. The composition according to claim 1, wherein the polycondensate comprises at least one silicone with a hydroxyl (OH) and/or carboxyl (COOH) group.

23. The composition according to claim 22, wherein the silicone has a weight-average molecular weight (Mw) between 300 and 20 000.

24. The composition according to claim 22, wherein the silicone is of the formula:

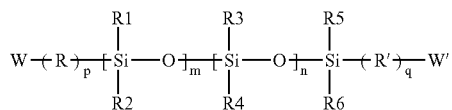

in which:
W and W' are, independently of one another, OH or COOH;
p and q are, independently of one another, equal to 0 or 1;
R and R' are, independently of one another, a hydrocarbon, divalent radical, saturated, unsaturated, or aromatic, linear, branched and/or cyclic; having 1 to 12 carbon atoms and optionally having in addition 1 or more heteroatoms selected from O, S and N;
or alternatively of formula —[$(CH_2)_xO]_z$— with x=1, 2 or 3 and z=1-10;
R1 to R6 are, independently of one another, selected from methyl, ethyl, propyl, isopropyl, butyl, pentyl, hexyl, octyl, decyl, dodecyl, octadecyl, cyclohexyl, phenyl, naphthyl, benzyl, phenylethyl, tolyl, and xylyl radicals;
m and n are, independently of one another, integers between 1 and 140, and are such that the weight-average molecular weight (Mw) of the silicone is between 300 and 20 000.

25. The composition according to claim 22, wherein the silicone is selected from one or more of α,ω-diol or α,ω-dicarboxylic polyalkylsiloxanes; α,ω-diol or α,ω-dicarboxylic polyarylsiloxanes; polyarylsiloxanes with silanol groups; polyalkylsiloxanes with silanol groups; and polyaryl/alkylsiloxanes with silanol groups.

26. The composition according to claim 22, wherein the silicone is selected from the α,ω-diol polydimethylsiloxanes of weight-average molecular weight (Mw) between 400 and 10 000.

27. The composition according to claim 22, wherein the silicone represents 0.1 to 15 wt. % of the total weight of the polycondensate.

28. The composition according to claim 1, wherein the polycondensate is obtained by reaction:
   of at least one polyol selected from, alone or mixed, 1,2,6-hexanetriol, trimethylolethane, trimethylolpropane, glycerol; pentaerythritol, erythritol, diglycerol, ditrimethylolpropane; xylitol, sorbitol, mannitol, dipentaerythritol and/or triglycerol;
   present in an amount from 10 to 30 wt. % relative to the total weight of the final polycondensate;
   of at least one non-aromatic monocarboxylic acid selected from, alone or mixed, caproic acid, caprylic acid, isoheptanoic acid, 4-ethylpentanoic acid, 2-ethylhexanoic acid, 4,5-dimethylhexanoic acid, 2-heptylheptanoic acid, 3,5,5-trimethylhexanoic acid, octanoic acid, isooctanoic acid, nonanoic acid, decanoic acid, isononanoic acid, lauric acid, tridecanoic acid, myristic acid, palmitic acid, stearic acid, isostearic acid, arachidic acid, behenic acid, cerotic (hexacosanoic) acid; cyclopentanecarboxylic acid, cyclopentaneacetic acid, 3-cyclopentylpropionic acid, cyclohexanecarboxylic acid, cyclohexylacetic acid, 4-cyclohexylbutyric acid;
   present in an amount from 30 to 80 wt. % relative to the total weight of the final polycondensate;
   of at least one aromatic monocarboxylic acid selected from, alone or mixed, benzoic acid, o-toluic acid, m-toluic acid, p-toluic acid, 1-naphthoic acid, 2-naphthoic acid, 4-tert-butyl benzoic acid, 1-methyl-2-naphthoic acid, 2-isopropyl-1-naphthoic acid;
   present in an amount from 0.1 to 10 wt. % relative to the total weight of the final polycondensate; and
   of at least one polycarboxylic acid or one of its anhydrides, selected from, alone or mixed, decanedioic acid, dodecanedioic acid, cyclopropanedicarboxylic acid, cyclohexanedicarboxylic acid, cyclobutanedicarboxylic acid, naphthalene-1,4-dicarboxylic acid, naphthalene-2,3-dicarboxylic acid, naphthalene-2,6-dicarboxylic acid, suberic acid, oxalic acid, malonic acid, succinic acid, phthalic acid, terephthalic acid, isophthalic acid, pimelic acid, sebacic acid, azelaic acid, glutaric acid, adipic acid, fumaric acid, maleic acid; cyclohexanetricarboxylic acid, trimellitic acid, 1,2,3-benzenetricarboxylic acid, 1,3,5-benzenetricarboxylic acid; butanetetracarboxylic acid, pyromellitic acid, phthalic anhydride, trimellitic anhydride, maleic anhydride and succinic anhydride;
   present in an amount from 5 to 40 wt. % relative to the total weight of the final polycondensate.

29. The composition according to claim 1, wherein the polycondensate is obtained by reaction:
   of at least one polyol selected from, alone or mixed, glycerol, pentaerythritol, and sorbitol present in an amount from 10 to 30 wt. % relative to the total weight of the final polycondensate;
   of at least one non-aromatic monocarboxylic acid selected from, alone or mixed, 2-ethylhexanoic acid, isooctanoic acid, lauric acid, palmitic acid, isostearic acid, isononanoic acid, stearic acid, and behenic acid present in an amount from 30 to 80 wt. % relative to the total weight of the final polycondensate;

of at least one aromatic monocarboxylic acid selected from, alone or mixed, benzoic acid, o-toluic acid, m-toluic acid, and 1-naphthoic acid present in an amount from 0.1 to 10 wt. % relative to the total weight of the final polycondensate; and of at least one polycarboxylic acid or one of its anhydrides, selected from, alone or mixed, phthalic anhydride and isophthalic acid present in an amount from 5 to 40 wt. % relative to the total weight of the final polycondensate.

30. The composition according to claim 1, wherein the polycondensate has at least one of the following characteristics:
   an acid number, expressed in mg of potassium hydroxide per g of polycondensate, greater than or equal to 1;
   a hydroxyl number, expressed in mg of potassium hydroxide per g of polycondensate, greater than or equal to 40;
   a weight-average molecular weight (Mw) of between 1500 and 300 000,
   a viscosity, measured at 110° C., between 20 and 4000 mPa·s,
   solubility in at least one solvent selected from isododecane, hydrogenated polyisobutene, isononyl isononanoate, octyldodecanol and $C_{12}$-$C_{15}$ alkyl benzoate, at 70° C.

31. The composition according to claim 1, wherein the polycondensate is present in an amount between 0.1 and 70 wt. % relative to the weight of the final composition.

32. The composition according to claim 1, wherein the cosmetically or pharmaceutically acceptable medium comprises at least one oily liquid phase, which comprises at least one compound selected from the oils and/or solvents of mineral, animal, vegetable or synthetic origin, carbon-containing/hydrocarbon-containing, fluorinated and/or siliconized, volatile or non-volatile, alone or mixed.

33. The composition according to claim 1, wherein the cosmetically or pharmaceutically acceptable medium comprises at least one oil and/or solvent selected from the group consisting of:
   1/esters of monocarboxylic acids with monoalcohols and polyalcohols corresponding to the following formula:
   R'$_1$—COO—R'$_2$ where:
   R'$_1$ represents a linear or branched alkyl radical with 1 to 40 carbon atoms, optionally having one or more ethylenic double bonds, optionally substituted and whose hydrocarbon chain can be interrupted by one or more heteroatoms selected from N and O and/or one or more carbonyl functions, and
   R'$_2$ represents a linear or branched alkyl radical with 1 to 40 carbon atoms, optionally having one or more ethylenic double bonds, optionally substituted and whose hydrocarbon chain can be interrupted by one or more heteroatoms selected from N and O and/or one or more carbonyl functions;
   2/vegetable hydrocarbon oils with high content of triglycerides comprising esters of fatty acids and of glycerol, where the fatty acids have chain lengths varying from $C_4$ to $C_{24}$, and the latter can be linear or branched, saturated or unsaturated;
   3/$C_6$-$C_{32}$ alcohols oleic alcohol, linoleic alcohol, linolenic alcohol, isostearyl alcohol, 2-hexyldecanol, 2-butyloctanol, 2-undecylpentadecanol and octyldodecanol;
   4/volatile or non-volatile, linear or branched hydrocarbon oils, of synthetic or mineral origin, selected from petroleum jelly, polydecenes, hydrogenated polyisobutenes squalane, perhydrosqualene, linear, branched and/or cyclic $C_5$-$C_{48}$ alkanes, and mixtures thereof;
   5/volatile or non-volatile silicone oils.

34. The composition according to claim 1, wherein the cosmetically or pharmaceutically acceptable medium comprises at least one oil and/or solvent selected from, isododecane, hydrogenated polyisobutene, isononyl isononanoate, octyldodecanol, phenyl trimethicone, $C_{12}$-$C_{15}$ alkyl benzoates, D5 (decamethylcyclopentasiloxane) and mixtures thereof.

35. The composition according to claim 1, wherein the cosmetically or pharmaceutically acceptable medium comprises at least one compound selected from thickening agents, waxes, colouring matter, antioxidants, perfumes, essential oils, preservatives, cosmetic actives, hydrating agents, vitamins, ceramides, sun filters, surfactants, spreading agents, wetting agents, dispersants, antifoaming agents, neutralizing agents, stabilizers, polymers and notably fat-soluble film-forming polymers, and mixtures thereof.

36. The composition according to claim 1, being in the form of a product for care and/or make-up of the skin of the body or of the face, the lips, the eyelashes, the eyebrows, the hair, the scalp or the nails; a suntan product or self-tanning product; a hair-care product notably for the colouring, conditioning and/or care of the hair.

37. The composition according to claim 1, being in the form of mascara, lipstick, lip gloss, blusher, eye shadow, or foundation.

38. The composition according to claim 1, comprising a polycondensate obtained by reaction:
   of 10 wt. % of at least one aromatic monocarboxylic acid having 7 to 11 carbon atoms, optionally in addition substituted with 1 to 3 saturated or unsaturated, linear, branched and/or cyclic alkyl radicals, which have 1 to 32 carbon atoms; and
   of 15 to 30 wt. %, relative to the total weight of the polycondensate, of at least one polyol containing 3 to 6 hydroxyl groups; and
   of 30 to 40 wt. %, relative to the total weight of the polycondensate, of at least one non-aromatic monocarboxylic acid, saturated, linear, branched and/or cyclic, containing 6 to 32 carbon atoms; and
   of 10 to 25 wt. %, relative to the total weight of the polycondensate, of at least one polycarboxylic acid, saturated, unsaturated or aromatic, linear, branched and/or cyclic, containing at least 2 carboxyl groups COOH and/or a cyclic anhydride of said a polycarboxylic acid;
   wherein the ratio of the number of moles of aromatic monocarboxylic acid to the number of moles of non-aromatic monocarboxylic acid is between 0.08 and 0.70.

39. A method of cosmetic treatment of the skin of the body or of the face, the lips, the nails, the hair and/or the eyelashes, comprising the application of a composition as defined in claim 1 to at least one of the face, the lips, the nails, the hair and/or the eyelashes.

40. A polycondensate obtained by reaction:
   of 10 to 30 wt. %, relative to the total weight of the polycondensate, of at least one polyol containing 3 to 6 hydroxyl groups;
   of 45 to 80 wt. %, relative to the total weight of the polycondensate, of at least one saturated, linear, branched and/or cyclic non-aromatic monocarboxylic acid, containing 6 to 32 carbon atoms;
   of 0.1 to 10 wt. %, relative to the total weight of the polycondensate, of at least one aromatic monocarboxylic acid containing 7 to 11 carbon atoms, optionally in addition substituted with 1 to 3 saturated or unsaturated, linear, branched and/or cyclic alkyl radicals, which contain 1 to 32 carbon atoms;

of 5 to 40 wt. %, relative to the total weight of the polycondensate, of at least one polycarboxylic acid, saturated, unsaturated, or aromatic, linear, branched and/or cyclic, containing at least 2 carboxyl groups COOH; and/or a cyclic anhydride of such a polycarboxylic acid, wherein the ratio of the number of moles of aromatic monocarboxylic acid to the number of moles of non-aromatic monocarboxylic acid is between 0.08 and 0.70.

41. A method of preparation of the polycondensates according to claim 40, comprising:
mixing the polyol and the aromatic and non-aromatic monocarboxylic acids,
heating the mixture under an inert atmosphere, firstly up to the melting point and then to a temperature between 150 and 220° C. until the monocarboxylic acids have been consumed completely, then
optionally cooling the mixture to a temperature between 90 and 150° C.,
adding the polycarboxylic acid and/or the cyclic anhydride, and optionally the silicone with hydroxyl or carboxyl groups, then
heating again to a temperature less than or equal to 220° C.

* * * * *

UNITED STATES PATENT AND TRADEMARK OFFICE
CERTIFICATE OF CORRECTION

| | |
|---|---|
| PATENT NO. | : 8,790,625 B2 |
| APPLICATION NO. | : 11/766118 |
| DATED | : July 29, 2014 |
| INVENTOR(S) | : Gerard Malle et al. |

Page 1 of 1

It is certified that error appears in the above-identified patent and that said Letters Patent is hereby corrected as shown below:

In the Specification

Column 29, Claim 41, line 15 "220° C." should read --220°C--;

line 18 "150° C." should read --150°C--.

Signed and Sealed this
Sixteenth Day of December, 2014

Michelle K. Lee
*Deputy Director of the United States Patent and Trademark Office*